United States Patent
Sohn et al.

(10) Patent No.: US 8,900,857 B2
(45) Date of Patent: Dec. 2, 2014

(54) DEVICES AND METHODS FOR TISSUE HANDLING AND EMBEDDING

(75) Inventors: Ian Emil Sohn, South Yarra (AU); Chester Henderson, Preston (AU); Timothy Brett McDonald, Greensborough (AU); Richard John Louis Gardner, Ascot Vale (AU)

(73) Assignee: Leica Biosystems Melbourne Pty Ltd, Mount Waverly (AU)

( * ) Notice: Subject to any disclaimer, the term of this patent is extended or adjusted under 35 U.S.C. 154(b) by 614 days.

(21) Appl. No.: 12/999,923

(22) PCT Filed: Jun. 18, 2009

(86) PCT No.: PCT/AU2009/000784
§ 371 (c)(1),
(2), (4) Date: May 2, 2011

(87) PCT Pub. No.: WO2009/152575
PCT Pub. Date: Dec. 23, 2009

(65) Prior Publication Data
US 2011/0201106 A1    Aug. 18, 2011

Related U.S. Application Data

(60) Provisional application No. 61/073,533, filed on Jun. 18, 2008.

(30) Foreign Application Priority Data

Jun. 18, 2008    (AU) ................................ 2008903106

(51) Int. Cl.
*C12M 3/00*    (2006.01)
*C12M 1/16*    (2006.01)

(52) U.S. Cl.
USPC .................................... 435/307.1; 422/561

(58) Field of Classification Search
None
See application file for complete search history.

(56) References Cited

U.S. PATENT DOCUMENTS

| 3,940,219 | A | 2/1976 | Pickett et al. |
| 6,387,653 | B1 | 5/2002 | Voneiff et al. |
| 6,843,962 | B2 * | 1/2005 | Haslam et al. ................ 422/65 |

FOREIGN PATENT DOCUMENTS

| EP | 0856729 B1 | 9/2002 |
| EP | 1293783 A2 | 3/2003 |
| JP | 2001-116669 A | 4/2001 |

(Continued)

OTHER PUBLICATIONS

International Search Report issued for corresponding PCT International Patent Application No. PCT/AU2009/000784.
English translation of Japanese Office Action issued Jun. 25, 2013 in corresponding Japanese Patent Application No. 2011-520274.

*Primary Examiner* — Edmund H. Lee
(74) *Attorney, Agent, or Firm* — Sughrue Mion, PLLC

(57) ABSTRACT

A mould and tissue cassette for automated embedding of tissue, and a method of operation are disclosed. The mould attaches to the cassette prior to embedding, and fits into a rack. The rack supports the mould holding the tissue cassette when the mould and cassette are in a first position. When the mould and cassette are moved to a second position, a projection on the rack separates the mould from the cassette, to facilitate easy removal. Also disclosed is a mould for a tissue cassette having projections for holding the mould to a rack, so that the tissue cassette is not in contact with the mould.

7 Claims, 8 Drawing Sheets

(56) References Cited

FOREIGN PATENT DOCUMENTS

| WO | WO-99/21658 | A1 | 5/1999 |
| WO | WO-2004/028693 | A1 | 4/2004 |
| WO | WO-2004/033307 | A2 | 4/2004 |
| WO | WO-2008/074073 | A1 | 6/2008 |

* cited by examiner

DEVICES AND METHODS FOR TISSUE HANDLING AND EMBEDDING

This application is a U.S. National Phase application under 35 U.S.C. §371 of International Patent Application No. PCT/AU2009/000784 filed Jun. 18, 2009, which claims the benefit of Australian Patent Application No. 2008903106 filed Jun. 18, 2008 and U.S. Provisional Patent Application No. 61/073533 filed Jun. 18, 2008, each of which is hereby incorporated by reference in its entirety.

FIELD OF INVENTION

The present invention relates to an improved device and method for handling and embedding tissue samples. In particular, the present invention relates to a device and method for automated handling and embedding of tissue samples for histological analysis.

BACKGROUND

Rapid and high quality preparation of samples within a histology laboratory, such as tissue sections on a microscope slide, is vital to correctly providing accurate analysis and diagnosis to a patient.

Typically, the workflow within a histology laboratory is as follows:

A biopsy sample is delivered in a container by courier from a doctor's surgery. The sample container is given an accession ID relevant to the laboratory, and is then passed on to the cut-up (grossing) area. Here, the sample is removed from the container, and cut up to excise pieces of interest. The pieces of interest are placed into one or more tissue cassettes, wherein the tissue specimen is held loosely in a cassette to segregate it from other samples. Each cassette is labelled so the tissue can be identified through the entire process. The next step requires the tissue specimen to be processed in a device such as a Leica ASP300. In such processing, the tissue is dehydrated using alcohol, and then infiltrated with paraffin wax to form a chemically stable block. Once stabilised and infiltrated with wax, the tissue is then taken from the cassette and oriented into a position appropriate for sectioning.

The orienting step is done manually and requires skilled operators. It can be time consuming to ensure that the tissue specimen is positioned correctly. This step typically involves taking the specimen out of the cassette, heating it to melt the infiltrated wax, selecting the correct size mould to use, dispensing a small volume of wax to the bottom of the mould, and carefully orientating the tissue specimen. It is critical that the specimen is accurately positioned, as the sectioning of the specimen must be in an appropriate plane to reveal the desired cells. The cassette fixture (holding fixture for the microtome) is then placed on the top of the mould, additional wax is dispensed to embed the fixture to the block and the paraffin block then cooled wherein the wax solidifies. The block is then removed from the mould and ready to be mounted on the microtome to be sectioned. The process, from the time a tissue sample arrives in the laboratory, to the point where a block is mounted on the microtome, adds significant delays to the provision of a diagnosis based on the tissue sample.

In order to decrease the time this process takes, several steps have been automated to various extents. However, other steps, such as the embedding process, have remained manual or semi automatic in a large number of laboratories. The manual embedding process is typically a slow process with an average of 40-60 samples per hour, and has also proven to be very labour intensive requiring the histotechnician to spend a large proportion of time handling individual cassettes. The repetitive nature of this task also exposes histotechnicians to the risk of repetitive strain injuries. Furthermore, as the process involves many manual steps, there is increased risk of errors occurring, such as mixing up tissue identity. Automation of processes in a histology laboratory is seen as beneficial to reducing turn around time, and can be assisted by automatic embedding.

There remains a need for improved methods and devices for automating the embedding process including handling tissue cassettes. The present invention is directed to overcoming or at least alleviating the problems associated with the prior art, or providing a useful alternative.

SUMMARY

In a first aspect, the present invention provides a sample carrier support comprising:
at least one receptacle for a sample carrier; the receptacle having a first position for locating the sample carrier, and a second position for separating one portion of the sample carrier from another portion.

In one form, the sample carrier comprises a tissue cassette and a mould.

In another form, the mould has a locator adapted to locate the mould to the receptacle in the first and second position, and releasable connector holding the tissue cassette to the mould while the mould and tissue cassette is in the first position.

In a further form, a method of embedding tissue is disclosed comprising the steps of:
a. Placing tissue into a mould and orienting the tissue in place
b. Attaching a cassette to the mould to form a carrier
c. Placing at least one carrier into a rack
d. Placing the rack into a bath of embedding material, filling the at least one carrier
e. Removing the rack from the bath and allowing the embedding material to solidify
f. Splitting the mould from the cassette by moving the carrier from a first position to a second position.

In a still further form, a mould for a tissue cassette is disclosed, comprising a well for receiving embedding media, connectors for releasably holding the mould to a tissue cassette, and a projection for defining a first position of the mould in relation to a support for the mould.

In a still further form, a mould for a tissue cassette is disclosed comprising a body having a well for holding tissue and embedding material, a first and second projection for holding the mould in place with respect to a support, and a connector for holding a tissue cassette. Preferably the locator and connector hold the tissue cassette away from the rack, to prevent embedding material from solidifying on the cassette after embedding.

BRIEF DESCRIPTION OF THE DRAWINGS

Preferred embodiments of the present invention are hereinafter described, by way of example only, with reference to the accompanying drawings, wherein.

DETAILED DESCRIPTION OF PREFERRED EMBODIMENTS

The device and method described hereafter are selected embodiments, and the present invention is not limited to these preferred embodiments. The arrangement of elements of the device and method in FIGS. 1-9 in no way limits the present invention. It is within the contemplation of the present invention to arrange or modify elements of the device and method in accordance with other design requirements, such as, the amount of space available to accomplish the device and method of this invention.

As used herein, the term "tissue sample" refers to an orientable tissue sample such as human, animal or plant tissue that is typically made up of a collection of biological cells and includes, but is not limited to, for example, biopsy samples, autopsy samples, surgical samples, cell smears, cell concentrates and cultured cells, and preparations made from microorganisms. The tissue sample generally includes any material for which microscopic examination of samples of the material prepared on microscope slides is desirable, and in particular to where the arrangement of the cells within a sample is to be maintained or controlled.

Figure 1:
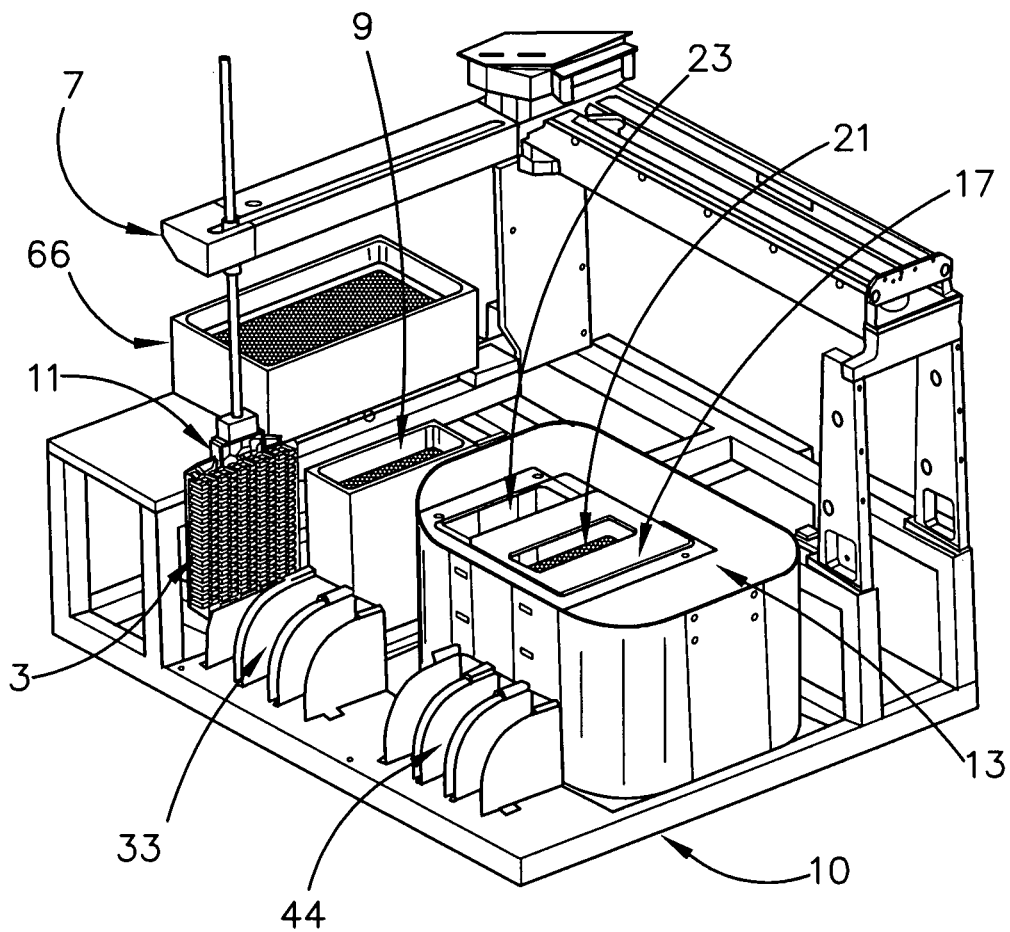
FIG. 1 shows an automated embedding device having a mount for engaging sample carrier supports.
Figure 3:
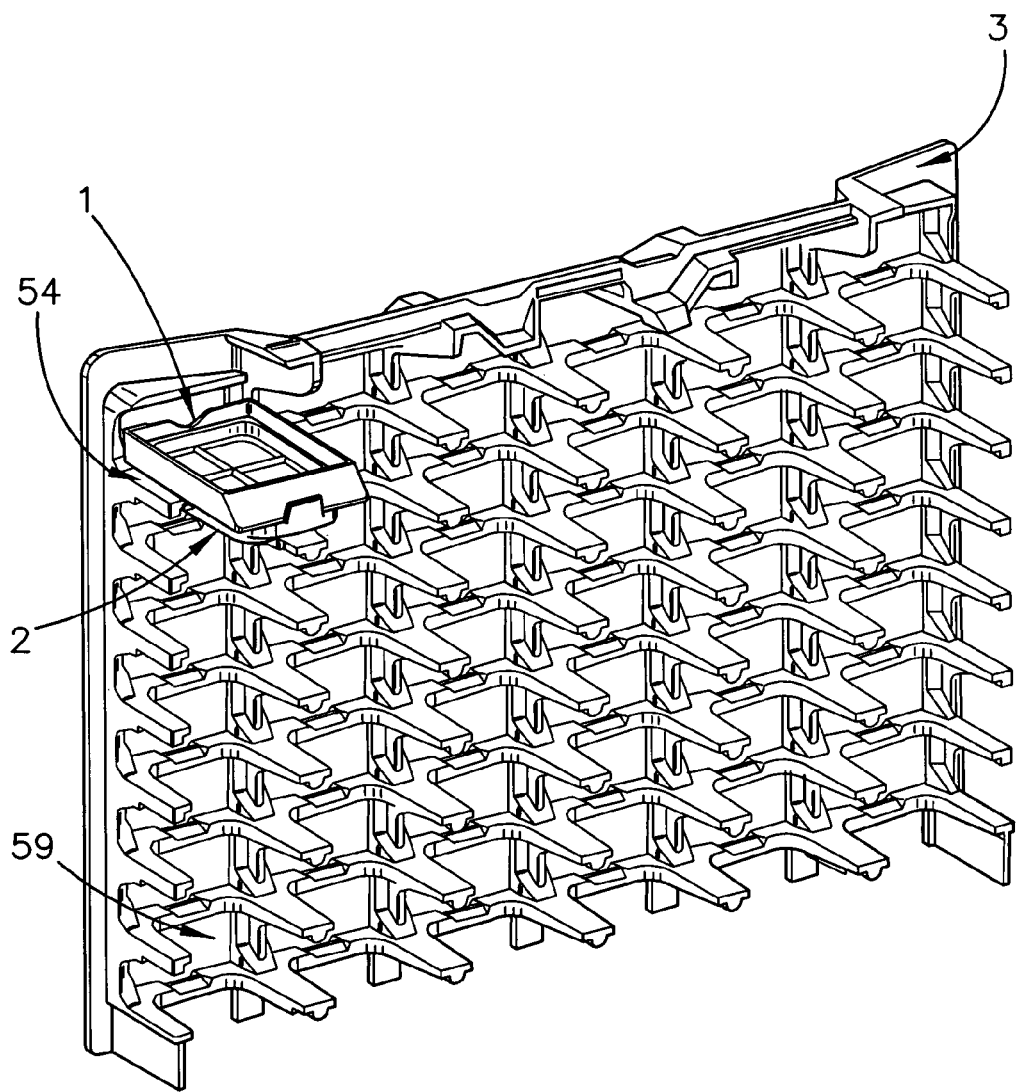
FIG. 3 shows a sample carrier support engaging the sample carrier of FIGS. 2a-2c.
Figure 4:
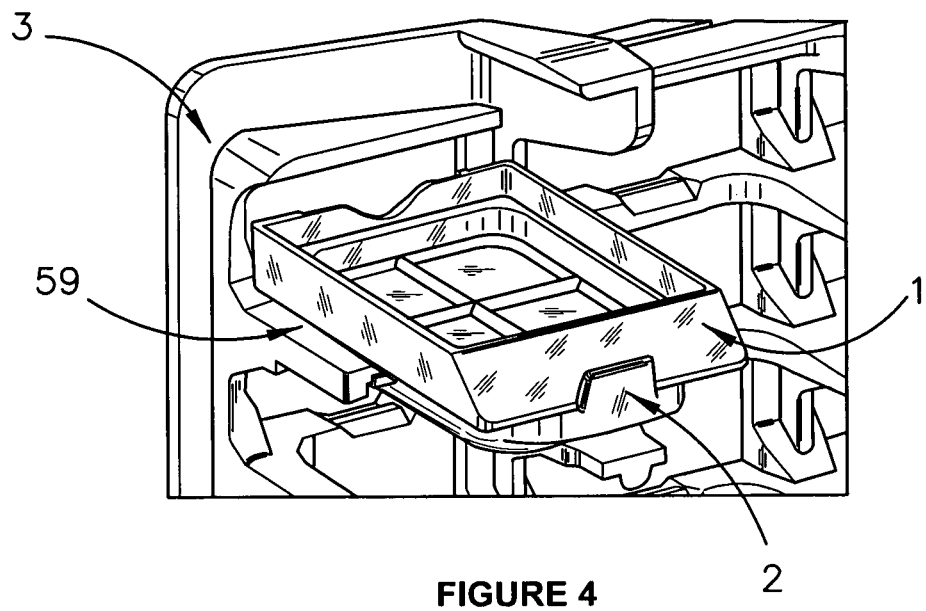
FIG. 4 shows an additional view of a section of the sample carrier support and sample carrier of FIG. 3.
Figure 5:
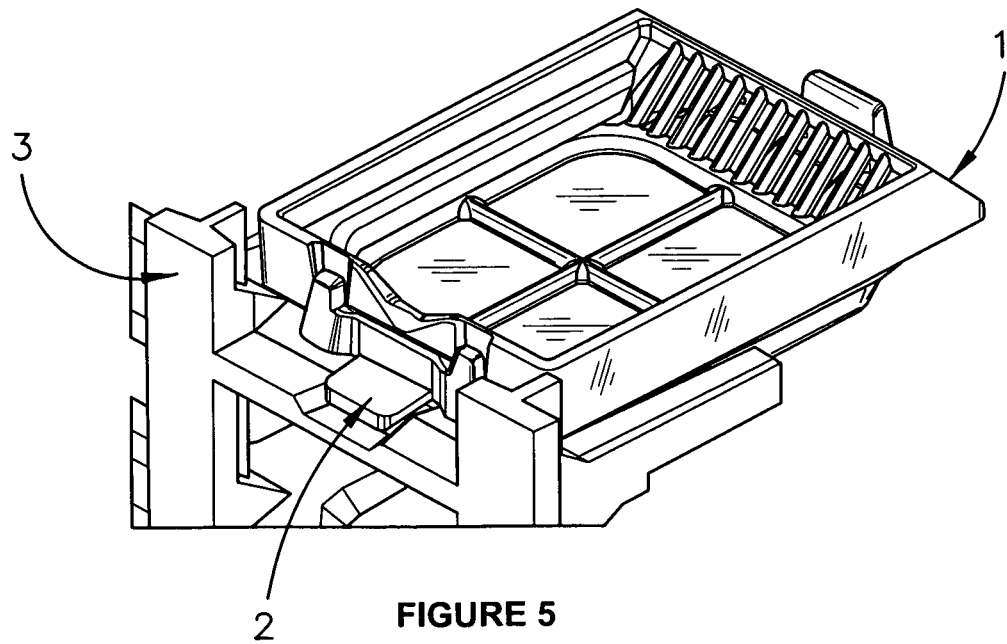
FIG. 5 shows a further view of a section of the sample carrier support and sample carrier of FIG. 3.
Figure 6:
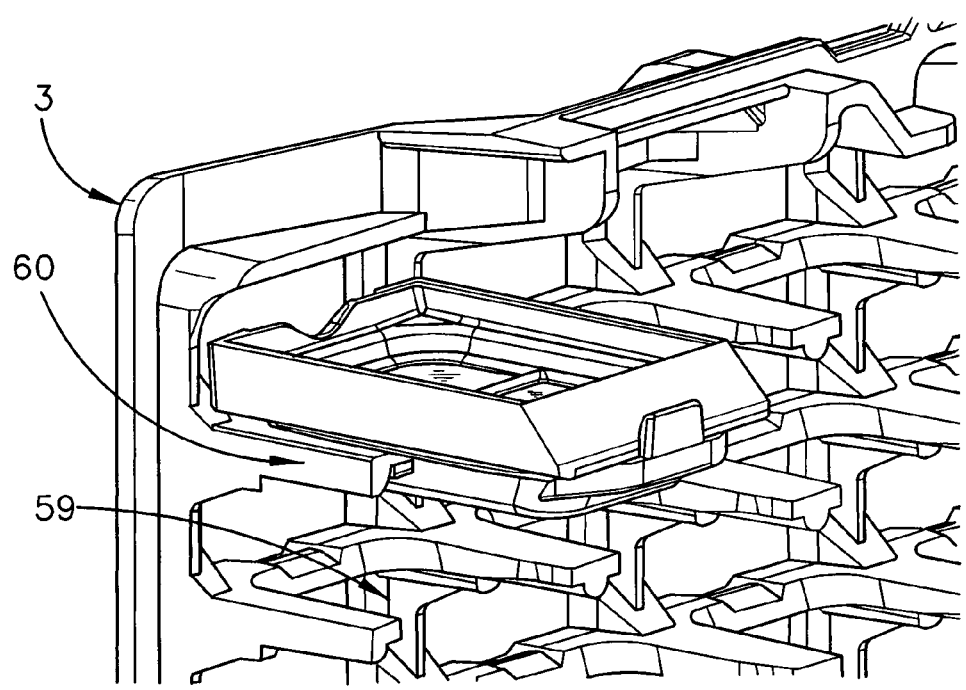
FIG. 6 shows an additional view of a section of the sample carrier support and sample carrier of FIG. 3.

Referring to FIG. 1, an automated embedding device 10 is provided comprising one or more input stations in the form of slots 33 and output stations in the form of slots 44 for receiving and/or storing one or more sample carrier supports 3, an embodiment of which is shown in FIG. 3. An example of a batch embedder is disclosed in International Patent WO 2008/074073 titled Device and Method for Tissue Handling and Embedding, filed by the applicant. The number of input slots 33 and output stations 44 provided may be modular and hold different numbers of sample carrier supports depending upon the throughput requirements of the laboratory. Input and output stations provide for random access and continuous operation of device 10. For example a number of sample carrier supports can be placed in the input slots and queued until ready for embedding, then stored in an output slot, providing the instrument with a continuous throughput of cassettes without human intervention. In the present embodiment, three input slots and three output slots are shown, however more or fewer may be provided. It is not necessary for the number of input slots to match the number of output slots.

Input slots 33 and output slots 44 may be provided with a sensor (not shown) to detect the presence of the sample carrier support 3 in the input slot 33 and output slot 44.

Embedding device 10 includes a transfer assembly 7 for transporting sample carrier support 3 to embedding chamber 9. The transfer assembly 7 may be any form of transfer mechanism, and include such components as a gantry, lead screw, carousel, electromagnet, cam arrangement, a Selective Compliant Assembly Robot Arm (SCARA), multi-axis arm, Cartesian robot, an XY robot or Z theta robot suitable for transporting the sample carrier support 3 to embedding chamber 9. In the present embodiment, the transfer assembly comprises an XYZ robot arm used to move sample carrier supports 3 from the input slots 33, to other areas of the device 1. The transfer may also be done manually by the user.

The transfer assembly 7 is provided with engaging means 11, such as a gripping mechanism for sample carrier support 3. In another embodiment, the engaging means 11 is a hook which the transfer assembly 7 positions under one end of sample carrier support 3, then moves vertically to engage the sample carrier support 3. In other embodiments, the engaging means 11 may comprise a system of electro-magnets, a suction cup, and/or jaws actuated by a solenoid, a motor, hydraulics and/or pneumatics. In one form, forklift style tines and a motorized clamp which moves down to prevent the rack 3 sliding off the tines may be used. The clamp can be positioned to hold the rack 3 securely, or backed off so the rack 3 can rotate on the tines.

As shown in FIG. 1, an embedding chamber 9 is provided that may be integral with the embedding device 10 as shown in FIG. 1. Embedding chamber 9 is configured to contain a volume of embedding media 18 and receive one or more sample carrier supports 3 as shown in FIG. 3. The chamber may be in fluid communication with a reservoir 66, which contains embedding material. In one form the embedding chamber 9 may be in the form of a wax bath adapted to take one or more sample carrier supports 3.

Any suitable embedding media may be used in accordance with the device 10. Paraffin is known and commonly-used as an embedding medium, however it will be appreciated that other embedding media, including but not limited to, TissueTek O.C.T., manufactured by Sakura Finetek, ester, microcrystalline cellulose, bees wax, resins or polymers, such as methacrylates, may also be used as embedding media. Suitable resins and polymers, including Araldite 502 Kit, Eponate 12™ Kit, and Glycol Methacrylate (GMA) Kit, are available from Ted Pella, Inc., Redding, Calif. Where a paraffin embedding material is used, the reservoir 66 and chamber 9 may employ heaters to melt the wax and/or keep the wax at an appropriate temperature. In one form the chamber 9 will have heaters to melt new wax placed into the reservoir 66.

In one embodiment, to cool the embedding media into a hardened block in the multiple sample carriers, the device 10 includes a cooling member such as a cooling chamber 13 comprising a cooling unit 15 (not shown). Access to the cooling chamber 13 may be via automatic sliding doors 17 located at each end of the cooling chamber 13. Cooling chamber 13 may be configured to cool one or more sample carrier supports 3 simultaneously. A number of different cooling members are possible.

In one embodiment (not shown), the sample carrier supports 3 may be left in a support so that ambient air surrounding the member cools the tissue supports and the embedding material held therein. Air may be forced past the tissue supports or natural circulation of air may be sufficient.

Figure 2A:
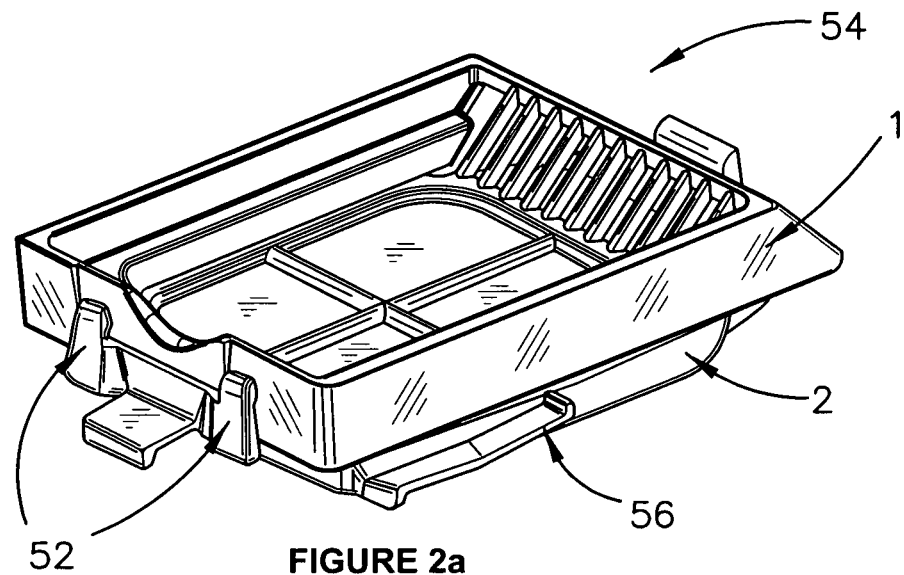
FIGS. 2a-2c are views of a sample carrier.
Figure 2B:
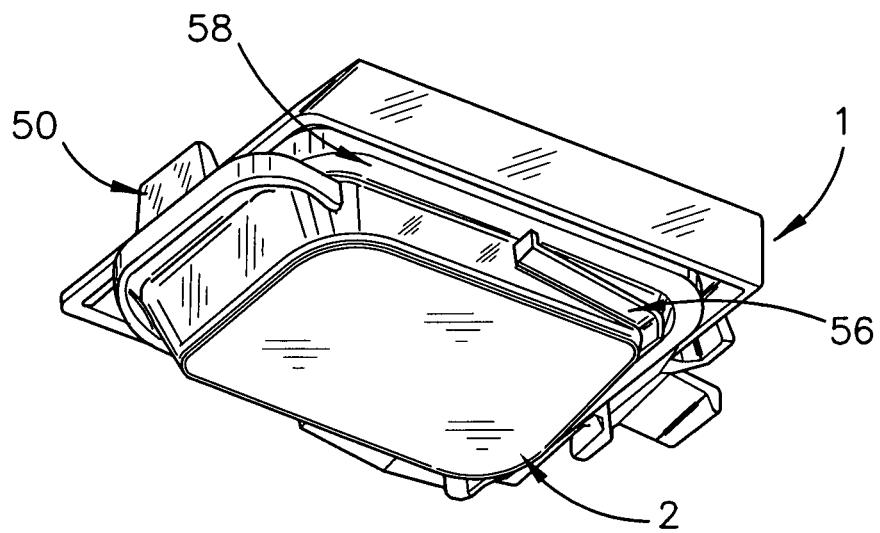
Figure 2C:
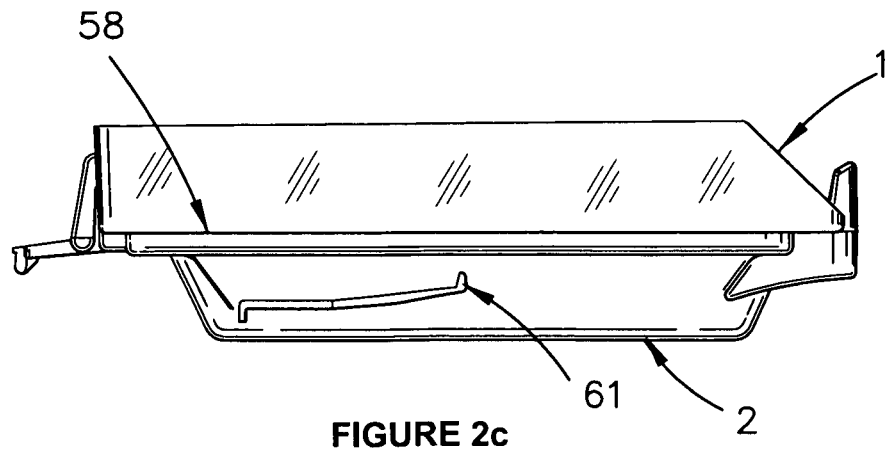

In FIGS. 2a, 2b and 2c, three views of a tissue cassette 1 attached to a mould 2 are shown. The tissue cassette 1 is attached to the mould 2 by a connector in the form of a clip or interference type fit at opposing ends of the cassette 1 and mould 2. The connector is releasable. In the present embodiment, a front tab 50 engages an edge of the cassette 1 to locate the mould 2 onto the support 3. At the rear of the support 3, further tabs 52 engage the cassette 1, thus holding the cassette 1 to the mould 2 to form a sample carrier 54. The sample carrier 54 is formed after a sample, such as tissue, is oriented on the mould 2, after which the cassette 1 may be attached to the mould 1 to form the carrier 54 which may travel through the tissue processing and embedding process described herein intact. The cassette 1 and mould 2 are joined in a manner that retains molten wax within the sample carrier when held substantially horizontal. The mould 2 can be seen with a body having a well for holding tissue and embedding material. In one form this involves the sides of the mould 2 being in contact with the sides of the sample carrier 3 to form a barrier to fluid leaks. After the embedding process has finished, the tissue will have been processed and the mould 2 will be full of wax. In order to cut samples from the tissue, the mould portion needs to be detached from the support. In order to achieve this, the following improvements have been developed.

In FIG. 3 a sample carrier support in the form of rack 3 is shown holding a carrier 54 formed from the cassette 1 and mould 2. The rack 3 can be seen to have a plurality of receptacles 59 adapted to receive and locate carriers, although only one carrier 54 is shown in FIG. 3 for clarity. The receptacles 59 may include arms 60 adapted to engage with the moulds 2 of the carrier 54. In FIGS. 2, 3 7A, 7B, 8A and 8B, rack locators in the form of guides 56 can be seen on the moulds 2, the guides 56 acting with an engagement portion of a flange 58 of the mould 2 to interact with the arms 60 of the receptacle 59 to locate the carrier 54. There are other methods of locating moulds and tissue supports with respect to the rack, which will be described below.

Figure 7A:
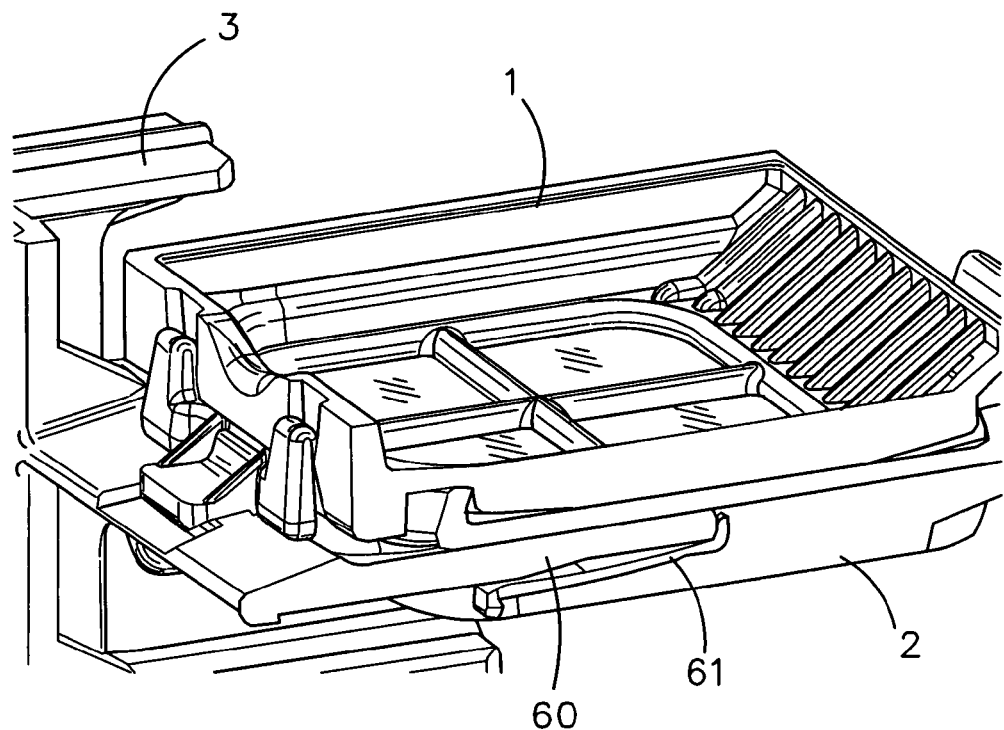
FIGS. 7a and 7b show a side view of the sample carrier support with the sample carrier in a first position.
Figure 7B:
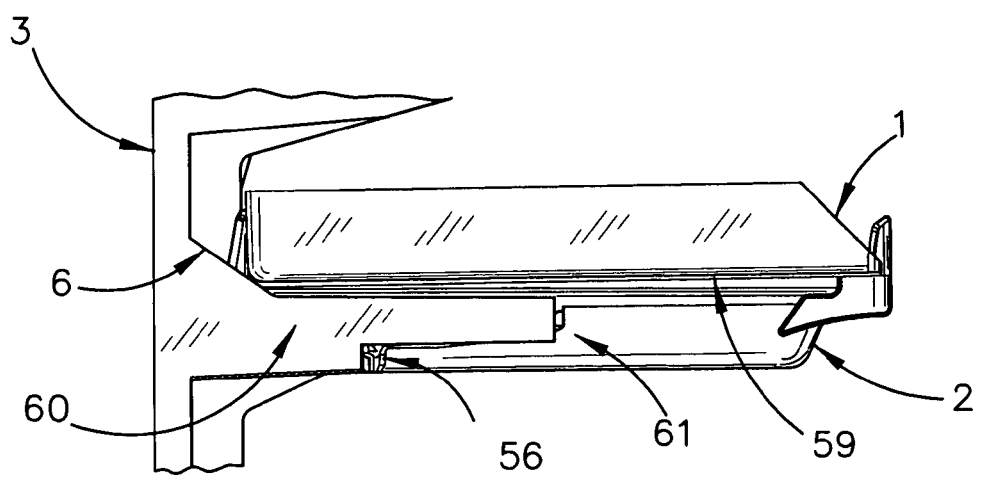
Figure 8A:
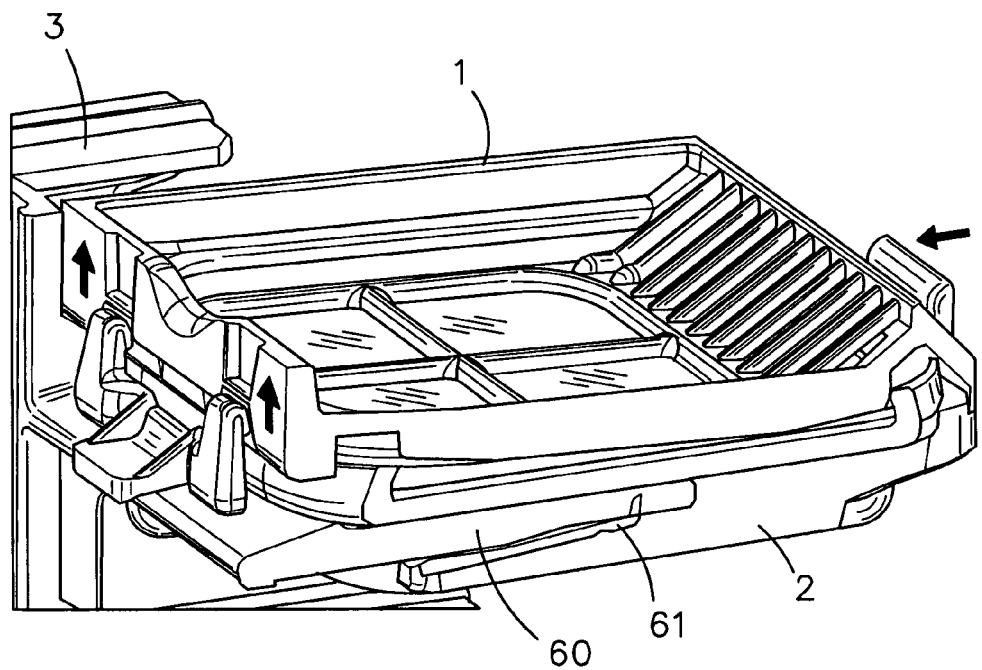
FIGS. 8a and 8b show a side view of the sample carrier support with the sample carrier in a second position.
Figure 8B:
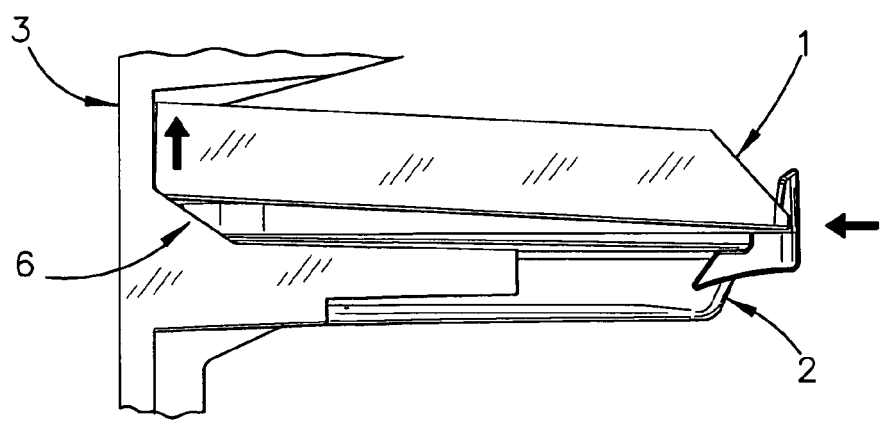

In FIGS. 7A and 7B, the carrier 54 formed from mould 2 with cassette 1 is mounted onto the arms 60 of the receptacle 59, where the flange 58 and guide 56 clip the carrier in place, positively locating it in a first position. A frangible/deformable leg 61 at the end of guide 56 provides an impediment to the carrier 54 being pushed further into the rack 3, and thus defines the first position. In FIGS. 8A and 8B, the carrier 54 has been pushed further into the rack 3, and the leg 61 has deformed to move out of the way of arms 60. The action of deforming or breaking the legs 61 provides positive feedback on the change of position and prevents the carrier 54 moving to the second position in the absence of a relatively significant force. In the first position, the carrier 54 may be securely located on arms 60 of the rack through the steps of processing and embedding. In FIGS. 8A and 8B, it can be seen that the carrier 54 has been pushed (in the direction of the arrow) further into the rack 3, to a second position whereby a portion 6 pushes the rear of the tissue cassette 1 upwards. The portion 6 is in the form of a ramp, in FIGS. 7B and 8B. The portion 6 is formed as a portion of the arm 60. The arm 60 is dimensioned so that the thickness in the vertical direction of the arm is smaller or substantially equal to the gap between the leg 61 and part of the tissue cassette 1. This allows the mould 2 and cassette 1, when pressed together as a carrier 54, to be mounted to the arm 60 and therefore the rack 3. The portion 6 is thicker than the gap between the cassette 1 and mould 2, and therefore when the cassette 1 and mould 2 are moved from the first position to the second position, the portion 6 forces the cassette apart from the mould. Thus the arms hold the mould but the portion 6 acts on the cassette 1 to separate the cassette 1 from the mould 2. In the present embodiment, as the mould 2 is constrained by the arms 60, guide 56 and flange 58, the mould 2 moves back into the rack 3, separating the rear tabs 52 from the carrier 1. The moulds 2 can be released together with the tissue cassettes 1 after separation, by pulling them (manually or with another mechanism) from the rack 3 in the reverse direction to which they were loaded. In one embodiment, during release, the tissue cassettes 1 and mould 2 are retained together by the front tab 50 but the wax connection has been broken, and they are now easily separated.

In FIG. 3 the supports 1 are arranged in an array configuration referred to herein as the rack. In other embodiments (not shown) the sample carrier support 3 may have only one receptacle 59, a line of receptacles or other configuration as appropriate.

As shown in FIGS. 7A, 7B, 8A and 8B, in one embodiment the mould 2 separates the cassette 1 from the arms 60 of the rack, creating a gap between the underside of the tissue cassette 1 and the arms 60. During embedding, the rack 3 is positioned substantially vertically so the moulds 2 trap embedding media around the samples contained therein. The gap between the cassettes 1 and the arms 60 removes the need to scrape cooled embedding media off the blocks of wax and cassettes before inserting them into the microtome, as the embedding media, for example wax, will adhere to the mould 2 and the arms 60, not the cassettes 1. Draining of the embedding media during operation of the device of the preferred embodiment of the present invention also results in a consistent level of wax in the sample carrier 54 independent of tissue and mould size. This is an advantage over a manual dispense method, where different volumes of embedding material are needed to fill the mould 2 and cassette 1, depending on tissue size in the mould.

Figure 9:
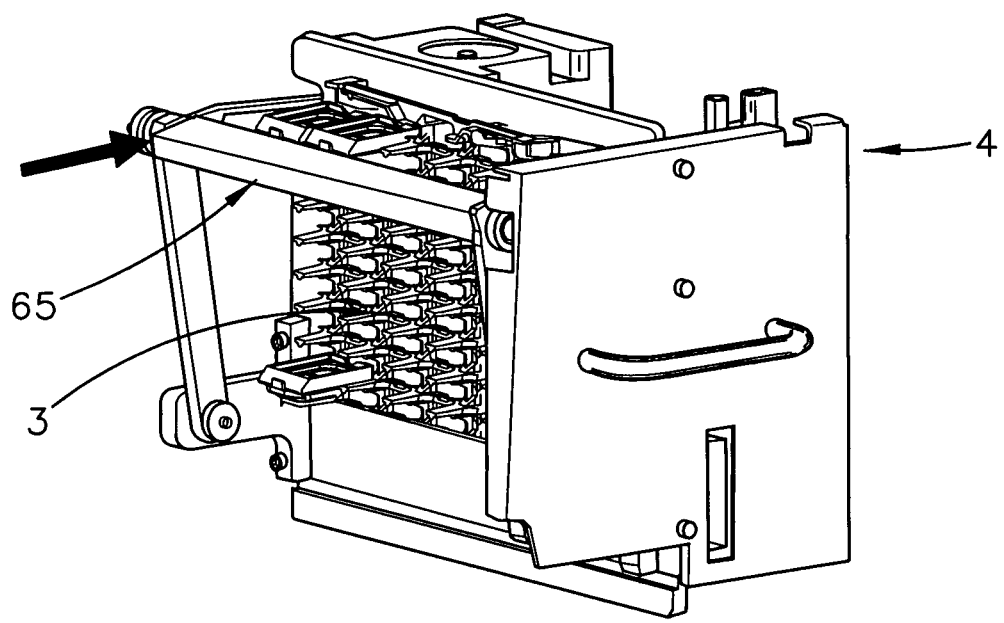
FIG. 9 shows schematic view of the sample carrier support of FIG. 2 in a splitter mechanism.

In FIG. 9, an example of a splitter mechanism 4 is shown. The splitter 4 includes a drive mechanism (not shown), which moves a bar 65 towards the rack 3. The rack 3 is loaded into the splitter mechanism 4 with the cassettes 1 oriented as shown in FIGS. 3-8B. As the bar moves towards the rack, it pushes the carriers from the first positions shown in FIGS. 7A to 7B to the second position shown in FIGS. 8A and 8B. In FIG. 9, the bar 65 is located at the top line of carriers in the rack 3. The bar 65 may move relative to the rack 3 to move the next line of carriers from the first position to the second position in the rack. This process may keep repeating until all the carriers are separated from the moulds 2. After separation, as the rack is in a vertical position, the carriers are retained in the mould 2 by gravity. The cassettes 1 are also retained on top of the moulds 2 by gravity and the front tab 50, and in use the mould 2 and cassette 1 would be withdrawn as a single unit. While the mould 2 and cassette 1 are still adjacent each other, the wax block attached to the cassette 1 has been separated from the mould 2, and therefore it is a simple matter to separate the cassette 1 from the mould 2.

It is possible to manually separate the cassette 1 from the mould 2 manually by pressing the mould 2 into the rack 3 in the same way the splitter mechanism would operate. This may be done by hand if desired, for example if manual embedding was desired. It is merely necessary to overcome the force of the leg 61 (in the present embodiment) to move the carrier (being mould 2 and cassette 1) from the first position to the second position.

In another embodiment, the splitter mechanism may have multiple bars to move more than one line or column of carriers from the first position to the second position. In another embodiment (not shown) the splitter mechanism may only do one carrier at a time.

Tissue supports of a variety of sizes can be inserted into the sample carrier support 3. In one embodiment, as shown in FIG. 3, the capacity of sample carrier support 3 is 48 tissue cassettes. The sample carrier support 3 may include an identifier, where the identifier may comprise features such as bar codes, RFID tags or OCR tags to allow the sample carrier support 3 to be identified and transported by the device 10. The identification may be a unique identifier for each sample carrier support 3, or it may be a general identifier designating a type of processing or embedding to be performed. The identifier may be automatically identified by a reader that may be associated with an embedding station or tissue processor or other apparatus.

In one embodiment, the sample carrier support 3 is compatible with the retort of a tissue processor instrument, such as a Peloris™ rapid tissue processor or Tissue Tek VIP tissue processor. For example the sample carrier support 3 may be adapted to fit within the confines of a tissue processor retort, and may be stackable so that more than one sample carrier support 3 fits efficiently within the retort while still allowing efficient processing of the tissue samples held therein. Embedding may be achieved by applying a sample carrier support 3 directly from a tissue processor to the automated embedding device 10.

The temperature of the wax bath may vary according to user requirements, but is typically kept at a temperature above the melting point of the embedding media. A typical wax bath temperature would be 65° C. when paraffin wax is used as an embedding media.

In an alternative embodiment, the cassette 1 may be located on the mould 2 by a variety of mechanisms. The mould 2 may be glued to the cassette 1 after orientation, using frangible glue designed to break upon application of a splitting force from the rack 3, when moved from a first position to a second position. Other forms of releasable attachment may be used, such as frangible features, friction-locking features, magnetism, zips, static electricity, Velcro, gaffer tape and blu-tack, provided the release mechanism for the releasable attachment allows the cassette 1 to be separated from the mould 2 by moving the cassette 1 and mould 2 from a first position to a second position.

While the invention has been described in connection with preferred embodiments and examples, it will be understood by those skilled in the art that other variations and modifications of the preferred embodiments described above may be made without departing from the scope of the invention. Other embodiments will be apparent to those skilled in the art from a consideration of the specification or practice of the invention disclosed herein. It is intended that the specification is considered as exemplary only, with the true scope and spirit of the invention being indicated by the following claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A sample carrier support comprising:
   more than one receptacle for a sample carrier, the sample carrier having a first portion and a second portion;
   each receptacle having a pair of arms projecting out from a support portion of the sample carrier, support and being adapted to locate a sample carrier,
   each receptacle having a first position for locating the sample carrier, and a second position for separating the first portion from the second portion,
   wherein in the first position, the sample carrier is mounted onto the arms, and in the second position, the sample carrier is positioned closer into the sample carrier support than in the first position.

2. The sample carrier support of claim 1 wherein the first portion of the sample carrier is a tissue cassette, and the second portion of the sample carrier is a mould.

3. The sample carrier support of claim 1 wherein the receptacle has a splitter for separating the first and second portions and wherein the splitter is a portion of an arm of the receptacle, the portion of the arm being dimensioned larger than a gap between the first portion and the second portion.

4. The sample carrier support of claim 1 wherein the second portion of the sample carrier has locating means adapted to locate the second portion to the receptacle in the first and second position, and means for releasably holding the first portion to the second portion while the second portion and first portion is in the first position.

5. A sample carrier support of claim 1 wherein a portion of the sample carrier support comprises a well for receiving embedding media, connectors for releasably holding the first portion of the sample carrier to the second portion of the sample carrier, and a projection for defining a first position of the first portion of the sample carrier in relation to a support for the second portion of the sample carrier.

6. The sample carrier support of claim 5 wherein the projection is deformable or frangible, to allow the first portion of the sample carrier support to move to a second position in relation to the support.

7. The sample carrier support of claim 1 wherein the arms each have an inclined portion with a thickness larger than a gap between the first portion and the second portion,
   the inclined portion configured to push the first portion away from the second portion as a result of the sample container being moved from the first position to the second position.

* * * * *